United States Patent [19]

Tirel et al.

[11] Patent Number: 4,732,981

[45] Date of Patent: Mar. 22, 1988

[54] 3-PYRAZOLIDINONE SALTS

[75] Inventors: Malcolm D. Tirel, Alderley Edge; William E. Long, Wilmslow, both of England

[73] Assignee: Ciba-Geigy AG, Basel, Switzerland

[21] Appl. No.: 32,721

[22] Filed: Apr. 1, 1987

Related U.S. Application Data

[62] Division of Ser. No. 834,985, Feb. 28, 1986, Pat. No. 4,687,846.

[30] Foreign Application Priority Data

Mar. 15, 1985 [GB] United Kingdom ................ 8506803

[51] Int. Cl.$^4$ .................. C07D 401/06; C07D 413/06
[52] U.S. Cl. .................................... 544/140; 546/211; 548/364
[58] Field of Search ........................ 544/140; 546/211; 548/364; 430/465

[56] References Cited

U.S. PATENT DOCUMENTS 3,247,201 4/1966 De Marle et al. ................. 548/364

FOREIGN PATENT DOCUMENTS 943928 12/1963 United Kingdom .
1006320 9/1965 United Kingdom .

Primary Examiner—Robert W. Ramsuer
Attorney, Agent, or Firm—Wenderoth, Lind & Ponack

[57] ABSTRACT

Salts of 1-phenyl-3-pyrazolidinones which are useful photographic silver halide developing agents.

4 Claims, No Drawings

3-PYRAZOLIDINONE SALTS

This application is a division of Ser. No. 834,985 filed Feb. 28, 1986, now U.S. Pat. No. 4,687,846.

The present invention relates to novel developing agents.

It is well know that certain pyrazolidinone compounds are useful as components of photographic developing compositions, as described, for example, in chapter 11 of the book "The Theory of the Photographic Process", 4th edition, edited by T. H. James and published by Macmillan. An example of such a compound is 1-phenylpyrazolidinone of the formula

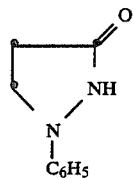
(1)

However, although widely used, developing agents of the pyrazolidinone class do suffer from certain disadvantages in their use. One disadvantage is that they only dissolve slowly in water, and thus elevated temperatures or prolonged stirring are necessary in order to make up solutions containing compounds such as the compound of the formula (1). A second disadvantage of such compounds is that they are susceptible to oxidation. It is known that said compounds may be rendered resistant to oxydation by use of a suitable protecting group to replace the labile N-H group. A particularly effective means of achieving this is described in GB No. 1 006 320, in which the N-H group is replaced by a substituted amino methyl group. This is an advantageous protecting group because it is removed by sulphite to regenerate the original pyrazolidinone compound. However, the protected pyrazolidinone compounds described in GB No. 1 006 320 still only dissolve slowly in water, and, particularly in the presence of other compounds, tend to produce oily or gummy deposits which do not dissolve in water even after a long period. Thus the protected developing agents of GB No. 1 006 320 can not be used in single bag developer compositions because of the formation of the oil or gummy deposits when water is added to dissolve the powdered mixture.

We have now prepared new salts of protected pyrazolidinone compounds which overcome these disadvantages. These new salts are readily soluble in water even in the presence of other components, and the resulting solutions are active as photographic developing compositions.

According to the present invention there are provided novel developing agents, which are 1-pyrazolidinone salts of the formula

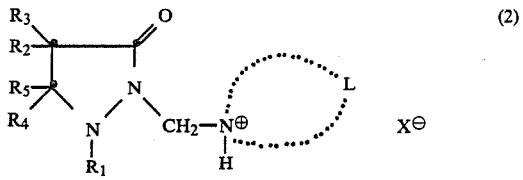

in which $X^\ominus$ is an anion, which may be organic or inorganic,

L represents the atoms necessary to complete a saturated ring or ring system, which may be substituted, $R_1$ is phenyl or substituted phenyl, $R_2$ and $R_3$ are each hydrogen, lower alkyl or substituted lower alkyl, $R_4$ and $R_5$ are each hydrogen, lower alkyl, substituted lower alkyl, phenyl or substituted phenyl.

By lower alkyl is meant an alkyl group containing 1 to 4 carbon atoms, for example methyl, ethyl, propyl, isopropyl, or butyl groups.

Suitable substituents for the alkyl groups $R_2$, $R_3$, $R_4$ and $R_5$ include hydroxyl, alkoxy, aryloxy, preferably phenoxy or amino groups.

Suitable substituents for the phenyl groups $R_1$, $R_4$ or $R_5$ include alkyl, alkoxy, chloro, hydroxyl or amino substituents. Preferably, the group $R_1$ is unsubstituted phenyl or p-tolyl.

Suitable anions $X^\ominus$ include halide ions such as chloride or bromide, and the anions of organic sulphonic acids, for example p-toluene sulphonate, benzene sulphonate, methane sulphonate, 3-hydroxypropane sulphonate and 5-sulphosalicylate.

Preferably, the groups $R_1$ are p-tolyl or p-anisyl and more preferably phenyl.

Suitable groups $R_2$ and $R_3$ are hydrogen, methyl, hydroxymethyl or hydroxyethyl.

Preferably, the groups $R_4$ and $R_5$ are both hydrogen.

Preferably, in order to keep the molecular weight down, the heterocyclic ring including the group L is a simple saturated ring such as pyrrolidine, piperidine or morpholine, or alternatively is a piperazine ring which has been substituted at the 4-position with another pyrazolidinone ring to give a compound of the formula

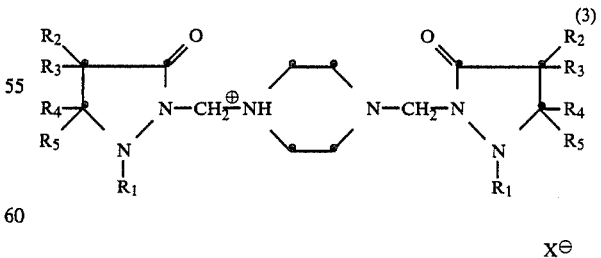

in which $R_1$, $R_2$, $R_3$, $R_4$, $R_5$ and $X^\ominus$ are as defined above.

Alternatively, both of the nitrogen atoms of a substituted piperazine compound may be used for salt formation, to give a compound of the formula

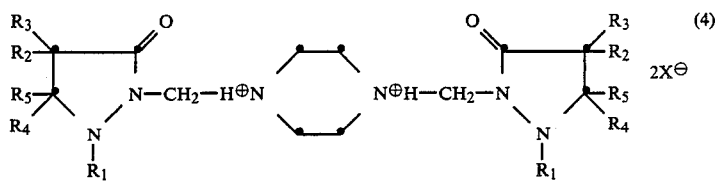

in which $R_1$, $R_2$, $R_3$, $R_4$, $R_5$ and $X^\ominus$ have the meanings assigned above.

Compounds of the formula (2) may be prepared by treatment of a compound of the formula

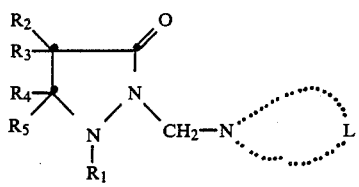

in which $R_1$, $R_2$, $R_3$, $R_4$, $R_5$, X and L have the meanings assigned above, with an acid HX in a suitable solvent and inducing crystallisation.

Suitable solvents include ethers such as tetrahydrofuran or dioxan, esters such as ethyl acetate, and ketones such as acetone. Preferably the compound of the formula (5) and the acid HX are used in a 1:1 stoichiometry; however, if it is desired to produce a bis-salt of formula (4) then a 1:2 ratio should be used. Solvents are chosen in which both the acid HX and the pyrazolidinone of formula (5) are readily soluble such that a one phase reaction may be used.

Compounds of formula (5) are described in GB No. 1 006 320, and may be prepared by the methods described therein, that is by reaction between a pyrazolidinone, formaldehyde, and a secondary amine.

Another embodiment of the present invention is a photographic processing composition containing a salt of the formula (2) together with other components commonly found in processing compositions, such as developing agents, for example, hydroquinone or substituted hydroquinone, bases or buffer systems such as for example sodium carbonate, or sodium tetraborate/boric acid, respectively, antioxidants or preservatives, for example sodium sulphite, restrainers for example sodiumd bromide, and antifoggants for example benzotriazole.

The following examples will serve to illustrate the invention.

EXAMPLE 1

Preparation of the compound of the formula

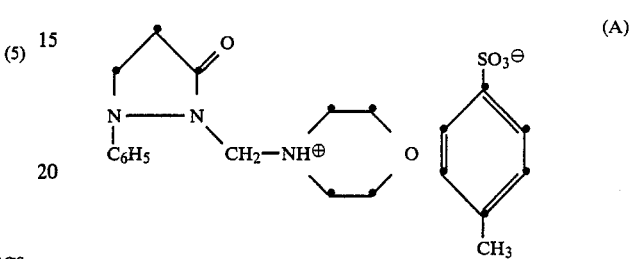

The precursor or 2-morpholino-methyl-1-phenyl pyrazolidinone was prepared as in Example 1 of GB No. 1 006 320. 3.2 grams of this compound was dissolved in acetone (15 ml) and p-toluene sulphonic acid monohydrate (2.5 g) was added. The solution was heated under reflux for 5 minutes, cooled in ice and the white crystalline solid product filtered off and washed with a little ether, yield 3.3 g (63%), melting point 139°–141° C.

EXAMPLE 2

Preparation of the compound of the formula

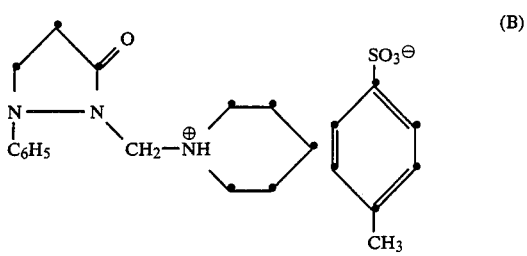

This compound was prepared in exactly the same fashion as the compound of the formula A, but using piperidine instead of morpholine. The product has a melting point of 126°–128° C.

EXAMPLE 3

Preparation of the compound of the formula (D) from the intermediate of the formula (C) which has the formula

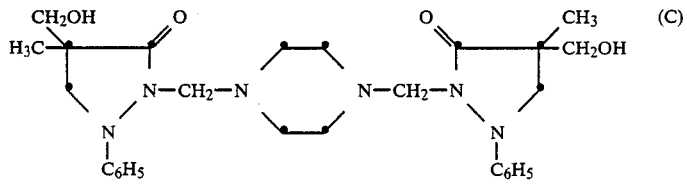

40% (W/W) Formalin (4.4 ml) was added to a solution of piperazine (2.15 g) in methanol (25 ml). After 10 minutes, 4-methyl-4-hydroxymethyl-1-phenyl-3- pyrazolidinone (10.3 g) was added and the yellow solution was heated under reflux for 12 hours. The solvents were evaporated and the solid product was recrystallised from ethyl acetate (80 ml), yield 8.45 g (65%), melting point 181°–185° C. The compound of the formula (D), which has the formula below was prepared from the intermediate of the formula (C).

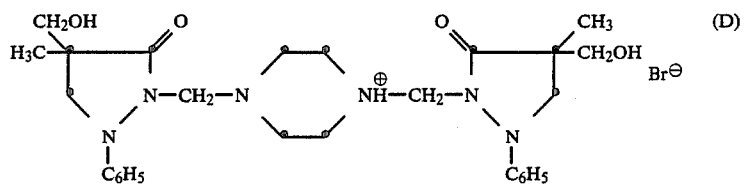

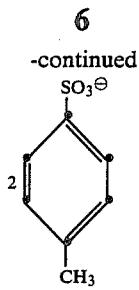

The intermediate of the formula (C) (1.0 g) in tetrahydrofuran (40 ml) and dichloromethane (50 ml) was mixed with 4.5% w/v hydrobromic acid in acetic acid (0.4 ml) at room temperature. After stirring for 1 hour, the solid compound of the formula (D) was filtered off and washed with a little ether, yield 0.65 g (57%), melting point 177°–181° C.

EXAMPLE 4

Other salts of the intermediate of the formula (C) were prepared by the same techniques:

| Compound of the formula | Anion | melting point |
| --- | --- | --- |
| (E) | p-toluene sulphonate | 95–101° C. |
| (F) | 5-sulphosalicylate | 113–117° C. |
| (G) | benzene sulphonate | 102–108° C. |

EXAMPLE 5

Preparation of the intermediate of the formula

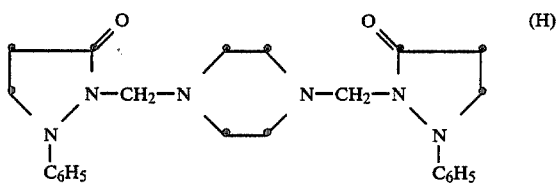

40% (W/W) Formalin (4.25 ml) was added to a solution of piperazine (2.15 g) in ethanol (50 ml) at 5° C. After 10 minutes, 1-phenyl-3-pyrazolidinone (8.1 g) was added and the yellow solution heated under reflux for 6 hours. The solvent was evaporated and the colourless crystalline product recrystallised from methanol, yield 6.93 g (64%), melting point 194°–195° C.

The compound of the formula

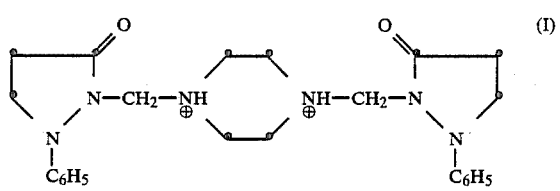

was prepared from the intermediate of the formula (H).

Intermediate of the formula (H) (0.75 g) was dissolved in tetrahydrofuran (50 ml) and a solution of p-toluene sulphonic acid monohydrate (0.69 g) (i.e. 2 equivalents) in tetrahydrofuran was added and the white precipitate filtered off and washed with ether, yield 1.12 g, melting point 117°–120° C.

EXAMPLE 6

Further salts (1:1) were prepared from the intermediate of the formula (H) of the general formula

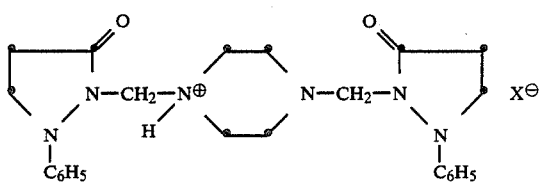

| Compound of the formula | Anion | melting point |
| --- | --- | --- |
| (J) | p-toluene sulphonate | 125–129° C. |
| (K) | benzene sulphonate | 142–148° C. |
| (L) | methane sulphonate | 159–162° C. |
| (M) | 3-hydroxypropane sulphonate | 113–117° C. |
| (N) | 5-sulphosalicylate | 85–90° C. |
| (O) | chloride | 164–167° C. |
| (P) | bromide | 168–172° C. |

In all the compounds of the formulae (A) to (P) n.m.r. spectroscopy was used to show the structure and the nature and stoichiometry of the salts.

EXAMPLE 7

Single bag developer powders were prepared containing the following ingredients:

| | |
| --- | --- |
| Hydroquinone | 1.5 g |
| Boric Acid | 0.8 g |
| Sodium Tetraborate | 2.0 g |
| Potassium Bromide | 0.3 g |
| Sodium Sulphite | 25.0 g–30 g (depending on salt used) |
| Pyrazolidinone Salt or | 0.05 g–0.5 g (depending on salt used) |

| | |
|---|---|
| -continued | |
| Pyrazolidinone Compound | 0.1 g |

The well known and widely used pyrazolidinone silver halide developing agents 1-phenyl-3-pyrazolidinone (Test I) and 4-hydroxymethyl-4-methyl-1-phenyl-3-pyrazolidinone (Test II) were also used as comparison compounds.

The pyrazolidinone type compounds used were the previously known compound of formula

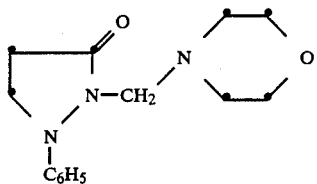

of Example 1 of GB No. 1 006 320 and the compounds of the formulae (A), (B) and (J) of the present invention.

The tests were carried out by mixing the above quantities of ingredients in a paper/foil laminate bag and heat-sealing.

Solubility tests were carried out by measuring the time taken for the contents of the bags to dissolve in 280 ml of water at 20° C. with gentle stirring. The results are given in the table below:

TABLE

| Sample containing compound of the formula | Time to Dissolve |
|---|---|
| (6), comparison | Does not at all dissolve - forms an oil |
| (A), present invention | 20 Seconds |
| (B), present invention | 2 Minutes |
| (J), present invention | 5 Minutes |
| Test I, comparison | Greater than 20 minutes |
| Test II, comparison | Greater than 20 minutes |

Thus the previously known compounds are not readily soluble at 20° C., whereas the compounds of the present invention dissolve rapidly at 20° C.

The photographic activity of the liquid developer compositions which comprised salts of formulae (A), (B) and (J) were compared with a freshly made up solution which contained 1-phenyl-3-pyrazolidinone which was dissolved up at 50° C. with constant stirring.

All these developing solutions made from powder compositions were very active silver halide developing solutions and as good as that made from the compound of the formula (1). Thus all the compounds of the present invention are of great use as silver halide developing agents and when formulated as single powder developer compositions give rapidly dissolving formulations.

What is claimed is:

1. A 1-phenyl-3-pyrazolidinone salt of the formula

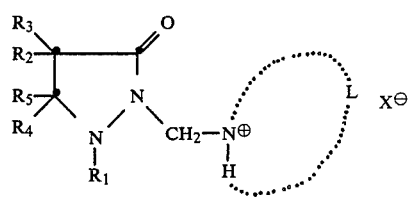

in which $X^{\ominus}$ is an inorganic anion,

L represents the atoms necessary to complete an unsubstituted pyrrolidine, piperidine or morpholine ring, $R_1$ is phenyl which is unsubstituted or substituted by alkyl, alkoxy, chloro, hydroxyl or amino, $R_2$ and $R_3$ are each hydrogen or lower alkyl which is unsubstituted or substituted or hydroxyl, alkoxy, aryloxy or amino, and $R_4$ and $R_5$ are each hydrogen, lower alkyl which is unsubstituted or substituted by hydroxyl, alkoxy, aryloxy or amino, or phenyl which is unsubstituted or substituted by alkyl, alkoxy, chloro, hydroxyl or amino.

2. A 1-phenyl-3-pyrazolidinone salt according to claim 1, wherein $R_2$ and $R_3$ are each hydrogen, methyl, hydroxymethyl or hydroxyethyl.

3. A 1-phenyl-3-pyrazolidinone salt according to claim 1, wherein $R_4$ and $R_5$ are each hydrogen.

4. A 1-phenyl-3-pyrazolidinone salt according to claim 1, wherein $R_1$ is phenyl, p-tolyl or p-anisyl.

* * * * *